(12) United States Patent
Yuasa et al.

(10) Patent No.: US 9,044,165 B2
(45) Date of Patent: Jun. 2, 2015

(54) OPTICAL TOMOGRAPHIC IMAGING METHOD AND OPTICAL TOMOGRAPHIC IMAGING APPARATUS

(75) Inventors: Takashi Yuasa, Sagamihara (JP); Mitsuro Sugita, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 264 days.

(21) Appl. No.: 13/133,250

(22) PCT Filed: Dec. 18, 2009

(86) PCT No.: PCT/JP2009/071719
§ 371 (c)(1),
(2), (4) Date: Jun. 7, 2011

(87) PCT Pub. No.: WO2010/084694
PCT Pub. Date: Jul. 29, 2010

(65) Prior Publication Data
US 2011/0234786 A1   Sep. 29, 2011

(30) Foreign Application Priority Data

Jan. 23, 2009 (JP) ................................ 2009-013069
May 22, 2009 (JP) ................................ 2009-124135

(51) Int. Cl.
*H04N 7/18* (2006.01)
*A61B 3/10* (2006.01)
(Continued)

(52) U.S. Cl.
CPC ............... *A61B 3/102* (2013.01); *A61B 5/0066* (2013.01); *A61B 5/0073* (2013.01);
(Continued)

(58) Field of Classification Search
CPC .... A61B 3/102; A61B 5/0066; A61B 5/0073; G01B 9/02019; G01B 9/02044; G01B 9/02027; G01B 9/02091; G01B 9/02087; G01B 2290/65; G01B 2290/45

USPC ................................................ 348/78
See application file for complete search history.

(56) References Cited

U.S. PATENT DOCUMENTS 5,321,501 A   6/1994   Swanson et al. ............... 356/345
6,198,540 B1   3/2001   Ueda et al. ...................... 356/479
(Continued)

FOREIGN PATENT DOCUMENTS

EP   1 775 545   4/2007
JP   08-252256   10/1996
(Continued)

OTHER PUBLICATIONS

Office Action issued Oct. 22, 2012, in counterpart Russian application 2011135047, with translation.
(Continued)

*Primary Examiner* — Andy Rao
*Assistant Examiner* — Nguyen Truong
(74) *Attorney, Agent, or Firm* — Fitzpatrick, Cella, Harper & Scinto

(57) ABSTRACT

An optical tomographic imaging method of picking up a cross-sectional image of an object comprises scanning a predetermined region of the object with spots of a plurality of measurement lights in the same direction so as to irradiate different positions of the object with different spots, detecting interference signals formed by the plurality of return lights reflected or scattered by the object and a plurality of corresponding reference lights reflected by a reference mirror, and executing an arithmetic process on the detected interference signals based on a displacement amount between the different spot positions using interference signals corresponding to at least two of the spots out of the respective interference signals. The region to be scanned has a length smaller than the sum of diameters of the spots in a direction perpendicular to the scanning direction.

14 Claims, 5 Drawing Sheets

(51) Int. Cl.
*A61B 5/00* (2006.01)
*G01B 9/02* (2006.01)

(52) U.S. Cl.
CPC ....... *G01B 9/02019* (2013.01); *G01B 9/02044* (2013.01); *G01B 9/02027* (2013.01); *G01B 9/02091* (2013.01); *G01B 9/02087* (2013.01); *G01B 2290/65* (2013.01); *G01B 2290/45* (2013.01)

(56) References Cited

U.S. PATENT DOCUMENTS

| | | | | |
|---|---|---|---|---|
| 6,341,036 | B1 | 1/2002 | Tearney et al. | 359/368 |
| 6,980,299 | B1 * | 12/2005 | de Boer | 356/497 |
| 7,859,682 | B2 | 12/2010 | Smith et al. | 356/497 |
| 2003/0004412 | A1 | 1/2003 | Izatt et al. | 600/425 |
| 2004/0076390 | A1 | 4/2004 | Dong Yang et al. | |
| 2005/0219544 | A1 | 10/2005 | Chan et al. | 356/497 |
| 2007/0076217 | A1 | 4/2007 | Baker et al. | 356/498 |
| 2007/0188707 | A1 | 8/2007 | Nanjo | 351/206 |
| 2007/0291277 | A1 | 12/2007 | Everett et al. | 356/497 |
| 2008/0015448 | A1 | 1/2008 | Keely et al. | 600/477 |
| 2008/0081950 | A1 | 4/2008 | Koenig et al. | 600/160 |
| 2008/0088852 | A1 | 4/2008 | Rogers et al. | 356/497 |
| 2008/0259275 | A1 | 10/2008 | Aoki et al. | 351/210 |
| 2008/0284981 | A1 | 11/2008 | Fercher | 351/221 |
| 2009/0021746 | A1 | 1/2009 | Toida et al. | 356/484 |
| 2011/0199615 | A1 | 8/2011 | Sugita | 356/456 |

FOREIGN PATENT DOCUMENTS

| | | |
|---|---|---|
| JP | 2875181 | 3/1999 |
| JP | 2000-193889 | 7/2000 |
| JP | 2004502957 A | 1/2004 |
| JP | 2007-151631 | 6/2007 |
| JP | 2008-508068 | 3/2008 |
| JP | 2008-520992 | 6/2008 |
| RU | 2145109 A | 1/2000 |
| WO | WO 2006/015717 | 2/2006 |
| WO | WO 2006/054116 | 5/2006 |
| WO | WO 2006/054975 | 5/2006 |
| WO | WO 2006/077107 | 7/2006 |
| WO | WO 2007/127291 | 11/2007 |
| WO | WO 2010/073655 | 7/2010 |
| WO | WO 2010/074279 | 7/2010 |
| WO | WO 2010/074321 | 7/2010 |

OTHER PUBLICATIONS

Japanese Office Action, dated Nov. 12, 2013, issued in Japanese counterpart application No. 2009-124135, with English-language translation (5 pages).

Chinese Office Action issued in counterpart application No. 200980155267.5 dated Jul. 29, 2014, along with its English-language translation (16 pages).

* cited by examiner

OPTICAL TOMOGRAPHIC IMAGING METHOD AND OPTICAL TOMOGRAPHIC IMAGING APPARATUS

TECHNICAL FIELD

The present invention relates to an optical tomographic imaging method and an optical tomographic imaging apparatus. More particularly, this invention relates to an optical tomographic imaging method and an optical tomographic imaging apparatus using optical coherence tomography for ophthalmologic diagnoses and other applications.

BACKGROUND ART

Optical coherence tomographic imaging methods and apparatus have been finding practical applications in recent years, applying techniques of low coherence interferometry and/or white light interferometry. In particular, optical tomographic imaging apparatus (optical interferometric measurement apparatus) for optical coherence tomography that utilizes multiwavelength optical interferometry can obtain cross-sectional images of samples with a high resolution so that such apparatus are becoming indispensable for obtaining tomographic images of fundi and retinas in the field of ophthalmology. Besides ophthalmology, dermatological cross-sectional observations and cross-sectional imaging of walls of digestive organs and circulatory organs, using endoscopes and catheters are under way. Optical coherence tomography will be referred to as OCT hereinafter in this specification.

Since OCT utilizes properties of light, an object can be measured with a high resolution of micrometers, or of the order of the wavelength of light, by means of OCT. However, while OCT allows fine measurements, a long measuring time is required to measure a wide region. Particularly, when the object of measurement is a part of a living body such as a human eye or the wall of a digestive organ that moves finely and randomly, the image obtained as a result of measurement can be distorted unless the measurement is conducted faster than the speed of the fine motion. Additionally, three-dimensional data need to be obtained from the object of measurement and an image of an arbitrarily selected cross section of the object needs to be synthesized for observation from the obtained data in order to examine the object more accurately. Then, the object needs to be measured very quickly.

In recent years, there is a rapid advancement in the technology of Fourier domain OCT apparatus that can obtain data in the direction of optical axis collectively if compared with time domain OCT apparatus. The Fourier domain OCT allows acquisition of data of a line in the direction of optical axis to be measured in cycles equal to tens of several kHz, which represents a speed of measurement that is several hundreds times of the speed of measurement of the conventional time domain OCT. For example, while the time domain OCT takes a second to obtain a cross-sectional image formed by 1,000×1,000 pixels by scanning a measurement light for a line in cycles equal to 500 Hz, the Fourier domain OCT takes only about 0.05 seconds because the Fourier domain OCT scans at a line measuring rate of 20 kHz.

With another high-speed measurement method, a broad region is divided into a plurality of sub-regions, which are then measured simultaneously by means of the same number of measurement lights. Japanese Patent No. 2875181 discloses an optical tomographic imaging apparatus that employs a plurality of light sources and the same number of photosensors and the individual photosensors are made to operate for the respective light sources by means of a common focusing optical system.

DISCLOSURE OF THE INVENTION

However, the above-cited Japanese Patent No. 2875181 describes a method of dividing the entire region to be scanned by the number of measurement lights to be scanned and hence the method entails processing difficulty that arises when the images obtained by dividing the entire region are put together to produce a complete single image of the entire region. Additionally, an optical tomographic imaging apparatus that employs a plurality of light sources and the same number of photosensors as disclosed in the above Patent Document gives rise to dispersion in terms of optical characteristics of the apparatus such as the quantities of light and the diameters of individual measurement lights. Then, the apparatus shows dispersion in terms of sensitivity and resolution. Furthermore, since each measurement light scans a single sub-region, the disclosed apparatus does not provide any improvement of sensitivity if compared with conventional apparatus that scan a region by a single measurement light.

In view of the above-identified problems of the prior art, the object of the present invention is to provide an optical tomographic imaging method and an optical tomographic imaging apparatus that can put images together by way of a simple and easy process and also can quickly acquire an OCT image with little dispersion in terms of sensitivity and resolution.

According to the present invention, there is provided an optical tomographic imaging method of picking up a cross-sectional image of an object to be measured by dividing each of divided lights emitted from a light source further into a measurement light and a reference light, guiding the plurality of measurement lights to the object while guiding the plurality of reference lights to a reference mirror, synthetically combining the plurality of return lights reflected or scattered by the object with the plurality of corresponding reference lights by means of a light-combining unit, and detecting interference lights, the method comprising:

a step of scanning a predetermined region of the object with spots of the plurality of measurement lights in the same direction by way of a scanning optical system, the predetermined region having a length in a direction perpendicular to the scanning direction, such that the length is smaller than the sum of diameters of the spots, to thereby irradiate different positions of the object with different spots of the plurality of measurement lights by way of an irradiation optical system;

a step of detecting interference signals formed by the plurality of return lights from the different positions of the object and the plurality of corresponding reference lights; and a step of executing an arithmetic process on the detected interference signals based on a displacement amount between different spot positions, using interference signals corresponding to at least two of the spot positions out of the interference signals corresponding to the respective spot positions, to thereby improve the signal-to-noise ratio.

In another aspect of the present invention, there is provided an optical tomographic imaging method for picking up a cross-sectional image of an object to be measured, by guiding a plurality of measurement lights to the object, synthetically combining the plurality of return lights reflected or scattered by the object with the plurality of corresponding reference lights by means of a light-combining unit, and detecting interference lights, the method comprising:

a step of scanning a predetermined region of the object with spots of the plurality of measurement lights in the same direction by way of a scanning optical system, the predetermined region having a length in a direction perpendicular to the scanning direction, such that the length is smaller than the sum of diameters of the spots, to thereby irradiate different positions of the object with different spots of the plurality of measurement lights by way of an irradiation optical system;

a step of detecting interference signals formed by the plurality of return lights from the different positions of the object and the plurality of corresponding reference lights; and a step of executing an arithmetic process on the detected interference signals based on a displacement amount between different spot positions, using interference signals corresponding to at least two of the spot positions out of the interference signals corresponding to the respective spot positions, to thereby improve the signal-to-noise ratio.

In still another aspect of the present invention, there is provided an optical tomographic imaging apparatus for picking up a cross-sectional image of an object to be measured by dividing each of divided lights emitted from a light source further into a measurement light and a reference light, guiding the plurality of measurement lights to the object while guiding the plurality of reference lights to a reference mirror, synthetically combining the plurality of return lights reflected or scattered by the object with the plurality of corresponding reference lights by means of a light-combining unit, and detecting interference lights, the apparatus comprising:

a scanning optical system adapted for scanning with a plurality of measurement lights in the same direction;

an irradiation optical system for irradiating different spot positions of an object with the plurality of scanning measurement lights;

an interference signal detecting unit for detecting interference signals formed by a plurality of return lights having irradiated different spot positions of the object and a plurality of corresponding reference lights; and a signal processing unit for executing an arithmetic process on interference signals detected by the interference signal detecting unit based on a displacement amount between the different spot positions, to thereby improve the signal-to-noise ratio.

In a further aspect of the present invention, there is provided an optical tomographic imaging apparatus for picking up a cross-sectional image of an object to be measured, by guiding a plurality of measurement lights to the object, synthetically combining the plurality of return lights reflected or scattered by the object with the plurality of corresponding reference lights by means of a light-combining unit, and detecting interference lights, the apparatus comprising:

a scanning optical system adapted for scanning with a plurality of measurement lights in the same direction;

an irradiation optical system for irradiating different spot positions of an object with the plurality of scanning measurement lights;

an interference signal detecting unit for detecting interference signals formed by a plurality of return lights having irradiated different spot positions of the object and a plurality of corresponding reference lights; and a signal processing unit for executing an arithmetic process on interference signals detected by the interference signal detecting unit based on a displacement amount between the different spot positions, to thereby improve the signal-to-noise ratio.

Thus, the present invention can realize an optical tomographic imaging method and an optical tomographic imaging apparatus that can put images together by way of a simple and easy process and also can quickly acquire an OCT image with little dispersion in terms of sensitivity and resolution.

Further features of the present invention will become apparent from the following description of exemplary embodiments with reference to the attached drawings.

BEST MODE FOR CARRYING OUT THE INVENTION

Now, an embodiment of optical tomographic imaging method and an embodiment of optical tomographic imaging apparatus for picking up a cross-sectional image of an object according to the present invention will be described below.

Figure 1:
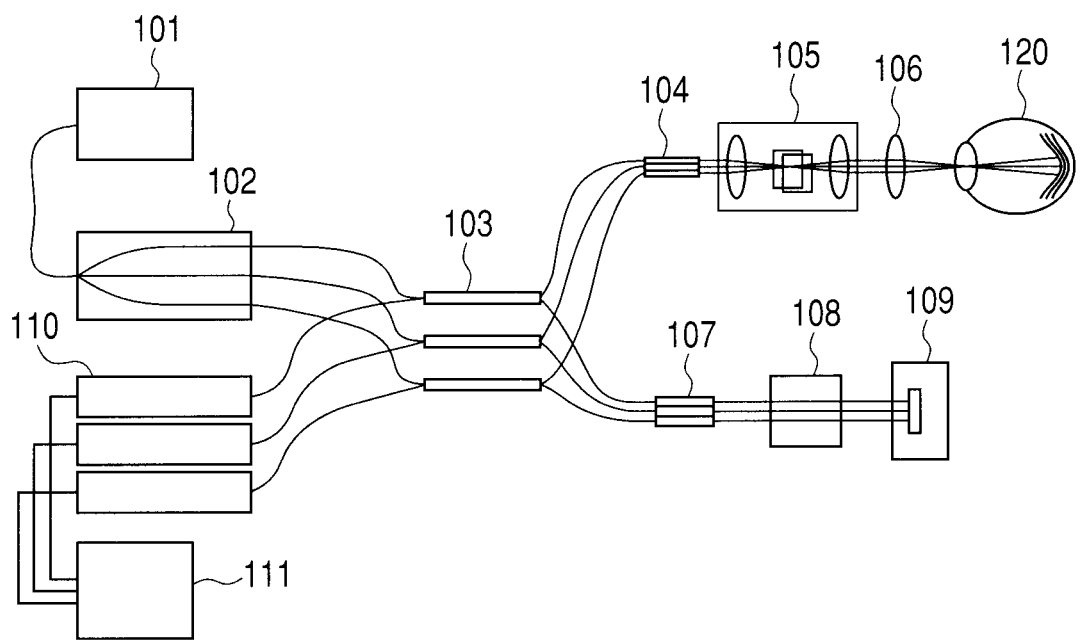
FIG. 1 is a schematic illustration of the configuration of the optical tomographic imaging apparatus of Example 1, which is an embodiment of the present invention.

FIG. 1 is a schematic illustration of the configuration of an optical tomographic imaging apparatus, which is an embodiment of the present invention.

In this embodiment, light emitted from a low coherence light source 101 is divided into a plurality of lights by a fiber beam splitter 102. Each of the plurality of lights is further divided into a measurement light and a reference light by a fiber coupler 103 and the plurality of measurement lights are then guided to a object to be measured while the plurality of reference lights are guided to a reference mirror.

The plurality of measurement lights to be guided to the object are emitted respectively from a set of fiber collimators 104 arranged at particular intervals. The plurality of measurement lights are moved by a scanning unit (scanning optical system) 105 to scan and irradiate the object (object to be measured) 120 respectively at different spot positions by way of an objective lens 106 of an irradiation optical system. The return lights produced by the object 120 as a result of reflection or scattering come back to the fiber couplers 103 by way of the same optical system.

On the other hand, the plurality of reference lights are emitted from another set of fiber collimators 107, reflected by a reference mirror 109 and returned to the fiber couplers 103. The reference lights are made to pass through a dispersion compensation glass 108 in order to make the quantities of wavelength dispersion thereof match those of the emitted reference lights.

Interference signals are produced at the fiber couplers 103 from the measurement lights reflected or scattered by the object 120 and returned to the fiber couplers 103 and the corresponding reference lights reflected by the reference mirror 109 and returned to the fiber couplers 103. The interference signals produced at the fiber couplers 103 are detected respectively as corresponding to the measurement lights by interference signal detecting units 110 in a step of detecting interference signals.

The interference signals that are detected in the above-described manner are then recorded in a recording/processing unit (signal processing unit) 111 in a signal processing step and subjected to an arithmetic process according to the displacement amounts of the different spot positions to thereby improve the signal-to-noise ratio.

Figure 2:
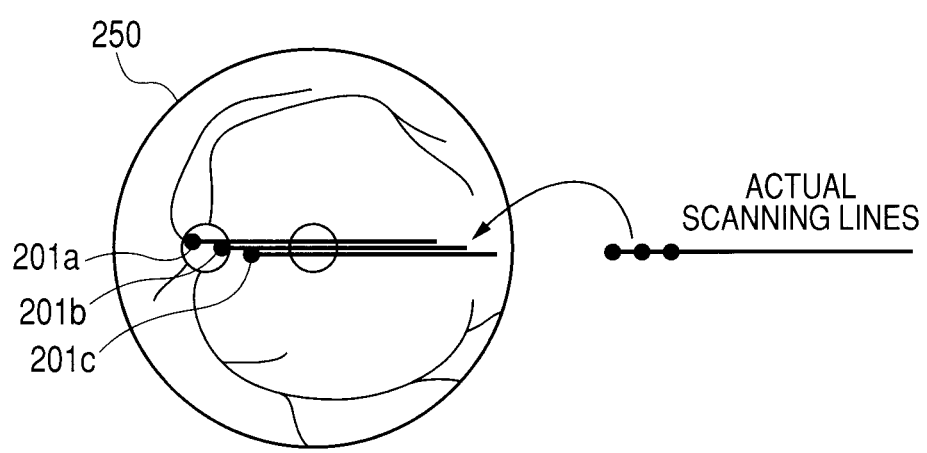
FIG. 2 is a schematic illustration of scanning spot positions and scanning lines in Example 1.

In FIG. 2, spots on an object 120 are indicated by solid circles and scanning lines are indicated by heavy lines. While the scanning lines are slightly separated from each other in FIG. 2 for easy comprehension, they are actually substantially laid one on the other in a direction perpendicular to them. For example, the spots of the plurality of measurement lights are moved by a scanning optical system to scan a predetermined region in the same direction so that the width of the region to be scanned in the direction perpendicular to the scanning direction of the spots of the measurement lights is smaller than the sum of the respective diameters of the spots.

Figure 3:
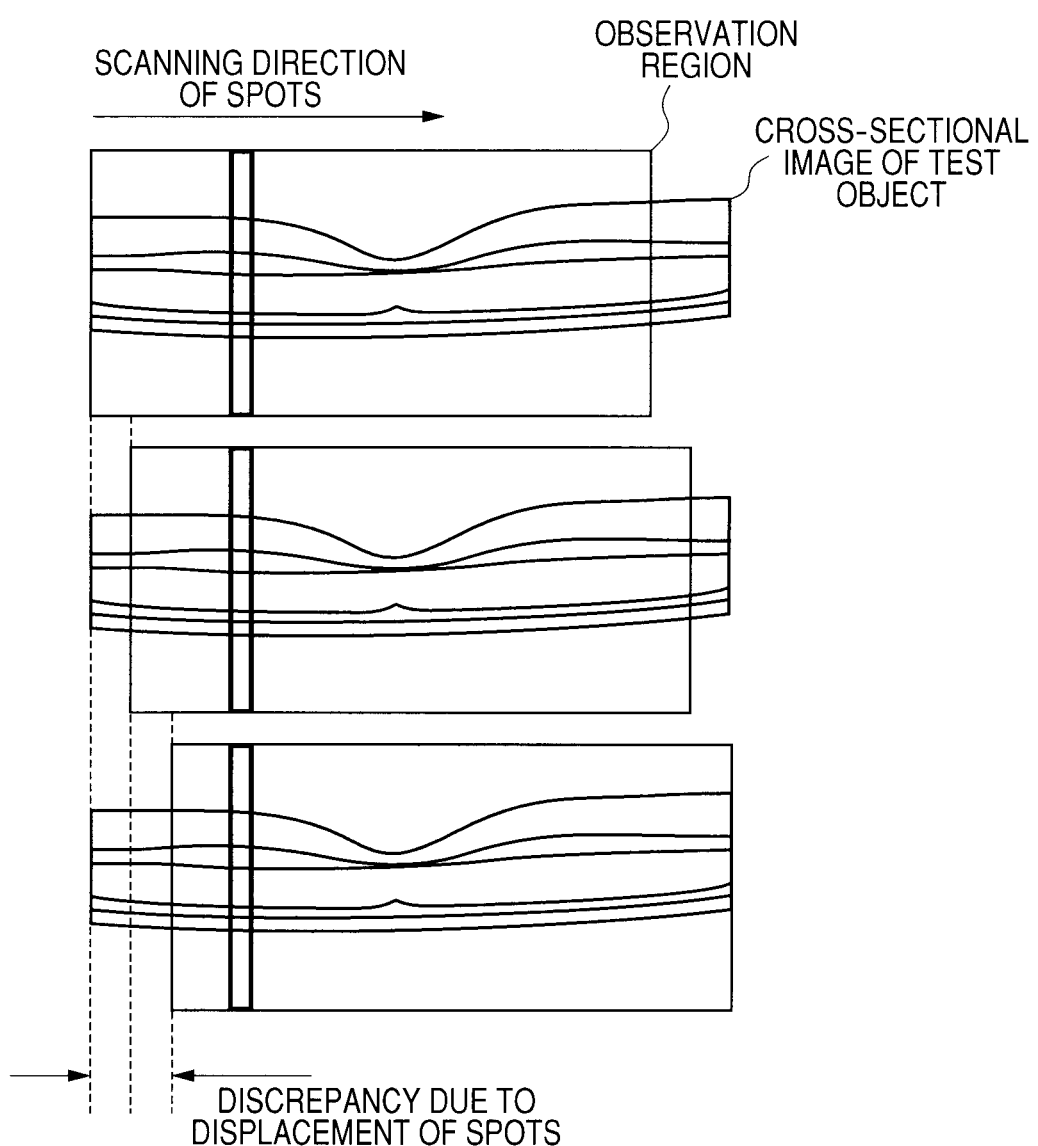
FIG. 3 is a schematic illustration of the relationship between the object and the measurement region of Example 1.

FIG. 3 is a schematic illustration of the relationship between the object and the regions to be measured by means of spots. The regions to be measured are displaced from each other due to the positional displacements of the spots. Thus, if compared with a signal obtained by a single spot for measurement, the signal-to-noise ratio can be improved by averaging the measurement data of substantially the same positions in the direction perpendicular to the scanning direction (each of the parts enclosed by heavy lines in FIG. 3), taking the positional displacements of spot positions into consideration.

An optical tomographic imaging apparatus as described above can find applications in various diagnostic apparatus and examining apparatus for observation of fundus or skin, for observation of a living body using an endoscope, for industrial quality control and so on.

The optical tomographic imaging method of the above-described embodiment may be provided as a program to be executed by a computer that is stored in a computer-readable memory medium (e.g., a flexible disk, a hard disk, an optical disk, a magneto-optical disk, a CD-ROM, a CD-R, a magnetic tape, a nonvolatile memory card, a ROM, an EEPROM or a Blu-ray disk).

Now, the present invention will be described further by way of examples.

Example 1

In this example, an optical tomographic imaging apparatus as illustrated in FIG. 1 is used to observe the retina of an eye. An SLD (super luminescent diode) having an output power of 20 mW, a central wavelength of 840 nm and a wavelength width of 45 nm is employed as low coherence light source 101. The light emitted from the light source 101 is equally divided into three lights by a 1-to-3 fiber beam splitter 102. Then, each of the lights is divided into a measurement light and a reference light by a corresponding one of three 50:50 fiber couplers 103. The measurement lights are made to proceed in parallel with each other by a set of fiber collimators 104 and are move to scan a predetermined region by a scanning optical system 105 that is formed by using a galvano scanner and a set of lenses. At that time, the scanning measurement lights are made to show a beam diameter of about 1 mm and proceed in parallel with each other via an objective lens 106 that operates as a member of an irradiation optical system so as to irradiate different positions respectively on the retina 120 of the eye.

FIG. 2 schematically illustrates a fundus image 250 of the retina 120. There are three spots 201a, 201b, 201c and three scanning lines on the fundus image 250. Since the irradiation optical system is so adjusted as to make the diameters of the incoming beams equal to about 1 mm, the diameters of the spots on the fundus are about 20 µm. The fiber collimators 104 have three fibers arranged at fiber intervals of 80 µm and showing a core diameter of 5 µm so that the spots are arranged at intervals of about 260 µm.

The three reference lights are made to proceed in parallel with each other by a set of fiber collimators 107, reflected by a reference mirror 109 by way of a dispersion compensation glass 108 and returned to the fiber couplers 103. Three interference signals are produced by the measurement lights reflected or scattered by the object 120 and returned to the fiber couplers 103 and the corresponding reference lights reflected by the reference mirror 109 and returned to the fiber couplers 103 and then made to enter respective spectral detection sections 110.

Each of the spectral detection sections 110 is formed by a spectral optical system having a 1,200/mm transmission grating and a line sensor with a pixel pitch of 14 µm, a pixel number of 2,048 and a line acquisition rate of 20 kHz to obtain wavelength spectrum data containing interference signals. The obtained data are recorded in a recording/processing unit 111 and OCT signals are acquired by subjecting the data to a Fourier transformation process. Further, a cross-sectional image of the retina 120 can be obtained by synchronizing the OCT signals with the frequency of the galvano scanner in the scanning optical system 105 when acquiring the OCT signals.

FIG. 3 illustrates the OCT measurement regions that correspond to the respective spots. Since the spots are arranged at intervals of 260 µm, adjacent measurement regions are displaced by about 260 µm from each other, which is about thirteen times of the spot diameter of 20 µm. A data row of $[X_1, X_2, X_3, \ldots, X_n, \ldots]$ is additionally prepared by way of an arithmetic operation of $X_n = A_{n+24} + B_{n+12} + C_n$, using the measurement data rows of $[A_1, A_2, A_3, \ldots, A_k, \ldots]$ where $A_k$ represents the k-th measurement data row arranged in the scanning direction as measured by means of the spot 201a, $[B_1, B_2, B_3, \ldots, B_l, \ldots]$ where $B_l$ represents the l-th measurement data row arranged in the scanning direction as measured by means of the spot 201b and $[C_1, C_2, C_3, \ldots, C_m, \ldots]$ where $C_m$ represents the m-th measurement data row arranged in the scanning direction as measured by means of the spot 201c that are obtained by means of the spots.

With the above-described arrangement, the data rows obtained at the same measurement position are subjected to an addition process, taking the positional displacements of spot positions into consideration, so that random noises can relatively be reduced to improve the signal-to-noise ratio of the obtained OCT image. Then, a three-dimensional image of the retina can be obtained by repeating the same measurement cycle, shifting the scanning lines on the surface of the fundus.

Thus, according to this example, it is only necessary to select positions for adding data in advance on the basis of the displacement amounts of the different spot positions and hence no complicated procedures for superposition such as correlation calculations for images are required. While spectral domain OCT using a line sensor is described here, a similar effect can be obtained by using time domain OCT or swept source OCT employing a wavelength scanning light source. Additionally, while the scanning lines are substantially laid one on the other in the direction perpendicular to the scanning direction in this example, a similar effect can be obtained so long as the scanning lines are displaced from each other within the diameter of the spots. Furthermore, an addition process is described above as a process for improving the signal-to-noise ratio of measurement data, a similar effect can be obtained by way of an averaging process such as $X_n = (A_{n+24} + B_{n+12} + C_n)/3$.

Thus, according to this example, the signal-to-noise ratio can be improved by means of an addition process or an averaging process, using the interference signals from the spots located substantially at the same position in the direction perpendicular to the scanning direction in the scanning region to be scanned by a scanning optical system. Additionally, if all the data from all the spots are not used, the signal-to-noise ratio can be improved by using the data on two of the spots. In other words, at least only the interference signals from two of the spots may be used out of the interference signals from all the spots of irradiation at the different spot positions.

Example 2

An example of forming an optical tomographic imaging apparatus by using a bulk optical system will be described below as Example 2. While the optical tomographic imaging apparatus of Example 1 is formed by using optical fibers, an optical tomographic managing apparatus can also be formed by using a bulk optical system.

Figure 4:
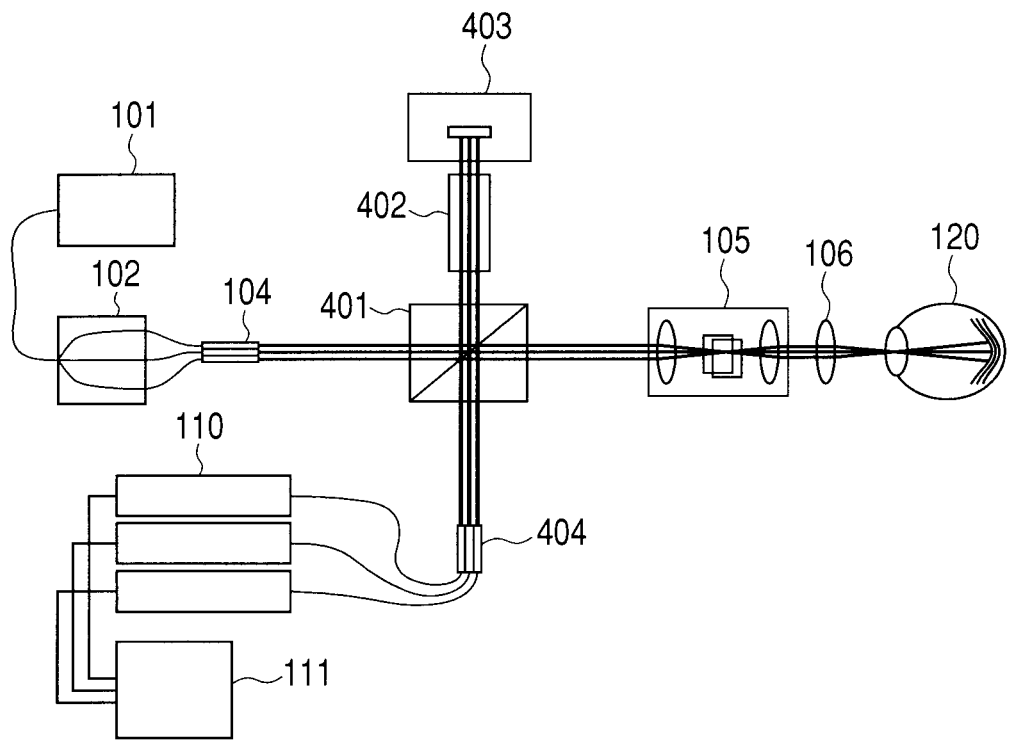
FIG. 4 is a schematic illustration of the configuration of the optical tomographic imaging apparatus of Example 2.

FIG. 4 is a schematic illustration of the configuration of the optical tomographic imaging apparatus of Example 2. The components of the optical tomographic imaging apparatus of this example that are same as those of the optical tomographic imaging apparatus illustrated in FIG. 1 are denoted respectively by the same reference symbols and will not be described any further.

As in Example 1, an SLD light source having an output power of 20 mW, a central wavelength of 840 nm and a wavelength width of 45 nm are employed as low coherence light source 101. The light emitted from the light source is equally divided into three lights by a 1-to-3 fiber beam splitter 102, which lights are made to proceed in parallel with each other by a set of fiber collimators 104. Each of the three lights is divided into a measurement light and a reference light by a cubic beam splitter 401. As in Example 1, the measurement lights are then made to show a beam diameter of about 1 mm and proceed in parallel with each other by a scanning optical system 105 and an objective lens 106 so as to irradiate different respective positions on the retina 120 of the eye.

The reference lights are reflected by a reference mirror 403 by way of a dispersion compensation glass 402 and returned to a set of fiber collimators 404. The interference signals produced by the lights are then made to enter respective three spectral detection sections 110 as in Example 1 and data is recorded in recording/processing section 111. While the configuration of the optical tomographic imaging apparatus of this example that is formed by using a bulk optical system differs from the configuration of the optical tomographic imaging apparatus of Example 1 that is formed by using optical fibers, the signal processing step of the apparatus of this example is similar to that of the apparatus of Example 1 because the lights are arranged similarly in the two examples.

While the arithmetic process is described above by way of addition process and averaging process, the arithmetic process to be executed for the purpose of the present invention is by no means limited to such processes. For example, a weighting and averaging process may alternatively be used for the purpose of the present invention. Then, the data rows may be weighted by respective values that correspond to the quantities of light of the spots for an averaging process. The quantities of light of the spots may show dispersion because manufacturing dispersion is observed in ordinary beam splitters and fiber couplers.

For example, the 1-to-3 fiber beam splitter 102 employed in this example shows maximum dispersion of 5% for the branching ratio. The quantities of light of the spots 201a, 201b and 201c in FIG. 2 were measured and found to be 705 µW, 730 µW and 700 µW respectively. Therefore, the variances in the signal intensity that reflect the variances in the quantity of light can be corrected to improve the signal-to-noise ratio by way of a calculation process of $X_n = (A_{n+24}/705 + B_{n+12}/730 + C_n/700)/3$, using the definition of data row descried above for Example 1.

Besides selecting the quantities of light for weighting indexes, a similar effect can be achieved by selecting values that correspond to the signal intensity levels of the spots or values that correspond to the noise levels of the spots. Still alternatively, indexes obtained by combining the quantities of light, the signal intensity levels and the noise levels may be used.

Example 3

An arrangement where the scanning optical system has a mechanism that can vary the scanning speed and is adapted to shift the scanning frequency according to the region to be scanned will be described for this example.

While no scanning speed is described for Examples 1 and 2 above, a scanning optical system 105 that employs a galvano mirror can shift the scanning frequency so as to use an arbitrarily selected frequency up to 500 Hz. Therefore, the scanning optical system can be used to serve for different objectives by appropriately shifting the scanning frequency according to the region to be measured such as an objective of measuring an object at high speed without lowering the signal-to-noise ratio or an objective of measuring an object at low speed to raise the signal-to-noise ratio.

Assume here a region to be measured of 6 mm×2 mm is measured by the measuring system of Example 1. If the spot diameter is 20 µm and an ordinary single spot OCT measurement technique is employed, a measurement time of 300× 100/20 kHz=1.5 seconds is required. In the case of this example, the same measurement operation can be completed within a measurement time of one third of the above measurement time with the same signal-to-noise ratio thanks to the process of raising the signal-to-noise ratio described above for Example 1 and using three spots so that an abnormal site, if any, can be detected with ease.

Figure 5:
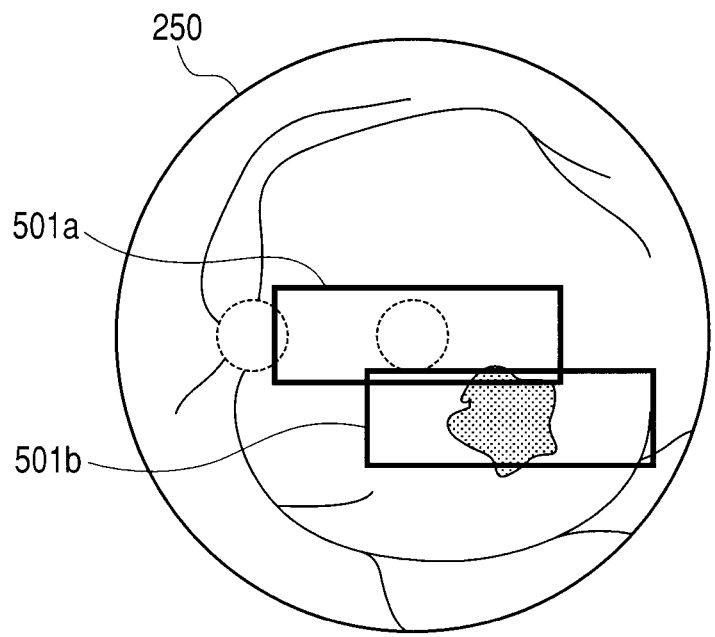
FIG. 5 is a schematic illustration of the measurement region of Example 3.

FIG. 5 is a schematic illustration of fundus 250. A region to be measured 501a of 6 mm×2 mm that is centered at macula on the fundus is roughly measured first. When the scanning frequency is raised to 100 Hz for the rough measurement, the required measurement time will be 0.5 seconds for reciprocating scanning. A site suspected for a disease that is located near an end of the region to be measured (the shaded part in FIG. 5) can be detected by this measurement cycle.

Then, a region to be measured 501b of 6 mm×2 mm that is centered at the site is measured for another time. Since the measurement this time is a scrutinizing observation, the scanning frequency is lowered to 33.3 Hz, which is one third of the previous frequency so that a measurement time of 1.5 seconds is required. While the measurement time is equal to that of a single spot OCT measurement cycle, the number of measurement spots is three times greater than that of a single spot OCT measurement. In other words, the same signal-to-noise ratio as the one obtained by a single spot OCT measurement conducted for a duration of time that is three times of the above duration can be achieved to detect and scrutinize an abnormal site.

While three spots are used in each of the above-described examples, a similar effect can be achieved by using two or more than two spots other than three.

Example 4

Figure 6:
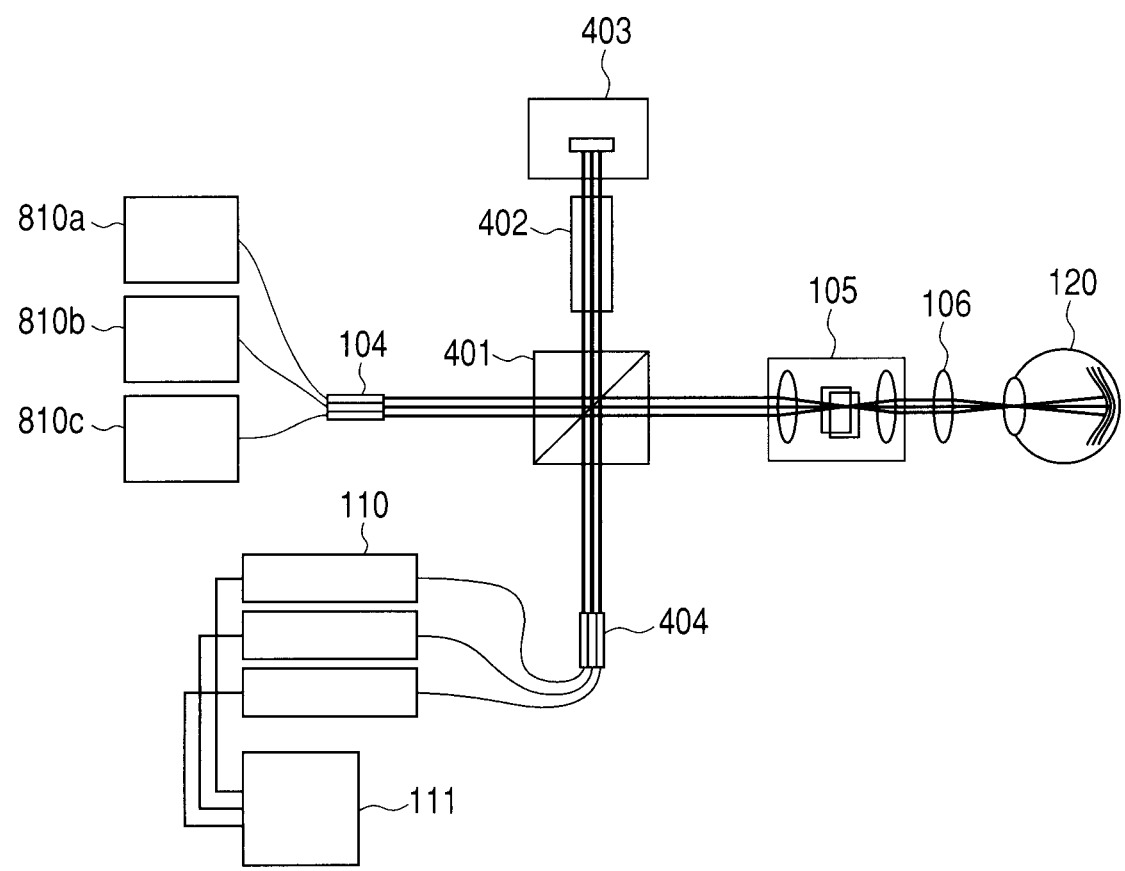
FIG. 6 is a schematic illustration of the configuration of the optical tomographic imaging apparatus of Example 4.

FIG. 6 is a schematic illustration of the configuration of the optical tomographic imaging apparatus of Example 4. The arrangement of FIG. 6 is the same as that of FIG. 4 except that the light source includes three SLD light sources 510a, 510b and 510c. The advantages of the present invention are secured even when different light sources are used for different lights as in this example. While three lights are used in this example, a similar effect can be achieved by using two or more than two beams other than three.

Example 5

Figure 7:
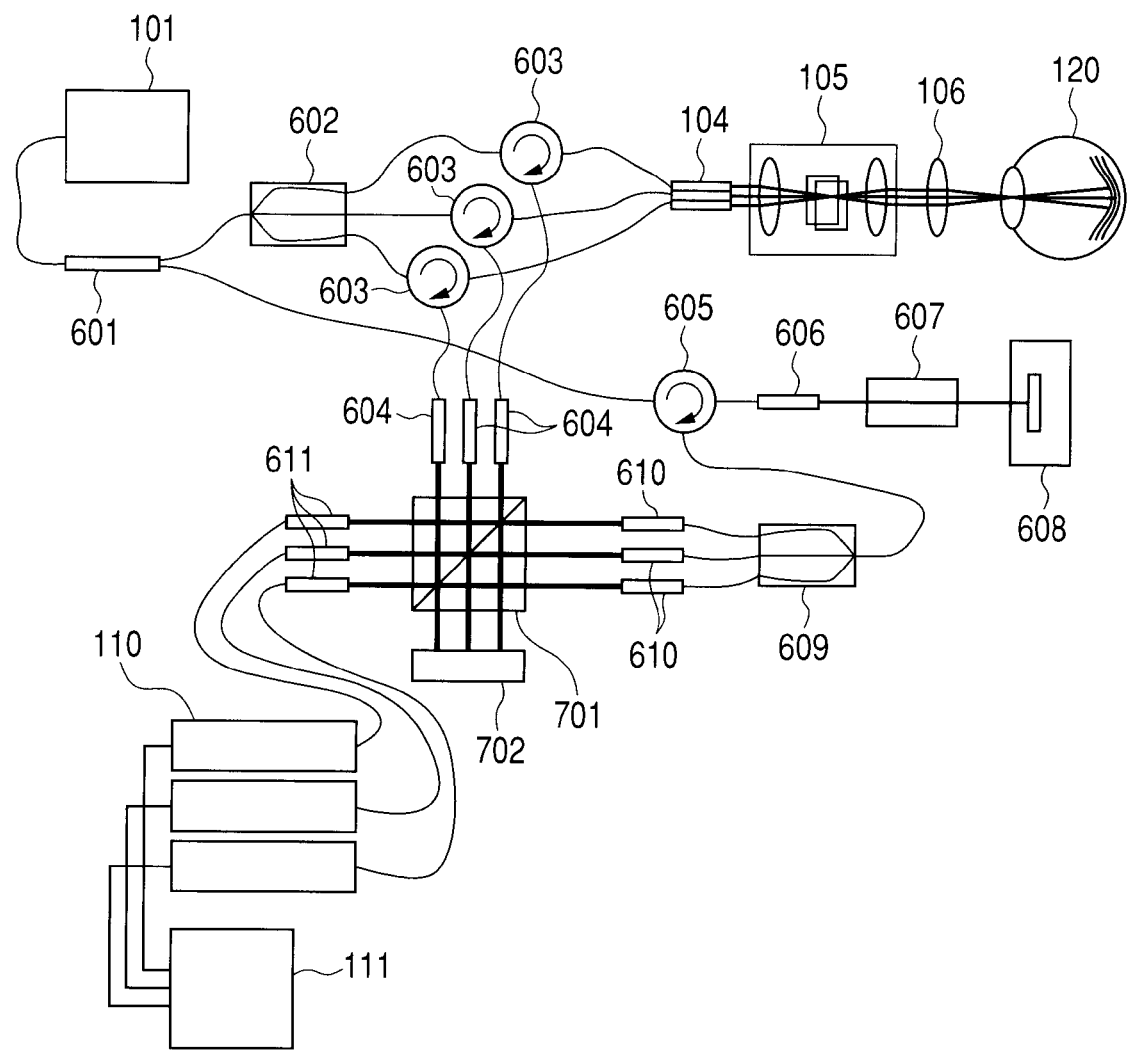
FIG. 7 is a schematic illustration of the configuration of the optical tomographic imaging apparatus of Example 5.

A Michelson interferometer is operated in each of the above-described examples, a Mach-Zehnder interferometer is employed in this example. FIG. 7 is a schematic illustration of the configuration of the optical tomographic imaging apparatus of this example that employs a Mach-Zehnder interferometer.

The light emitted from the SLD light source 101 is split into a measurement light and a reference light by a 1-to-2 fiber beam splitter 601. The measurement light is equally divided into three lights by a 1-to-3 fiber beam splitter 602, which are then input to respective optical circulators 603. After passing through the respective optical circulators 603, the lights are made to proceed in parallel with each other by three fiber collimators 104 and irradiated onto respective spot positions on the retina 120 of an eye by means of a scanning optical system 105 that is formed by a galvano scanner and a scanning lens and an objective lens 106. The three lights are so adjusted as to scan a region that is the same as that of Example 1.

The return lights reflected or scattered by the retina 120 are returned to the respective optical circulators 603 by way of the same optical system. The lights returned to the optical circulators are then output not to the side of the fiber beam splitter 602 but to the side of the fiber collimators 604 due to the properties of the optical circulators. These return lights are then made to proceed in parallel with each other by fiber collimators 604 and input to a beam splitter 701.

On the other hand, the reference light is made to pass through an optical circulator 605 and emitted from a fiber collimator 606. Then, the reference light is made to pass through a dispersion compensation glass 607 and reflected by a reference mirror 608 before the light thereof is returned to the optical circulator 605. The return light is output to the side of the 1-to-3 fiber beam splitter 609 by the optical circulator 605 and equally divided into three lights. The three reference lights produced as a result of equally dividing the original reference light by three are then made to proceed in parallel with each other by fiber collimators 610 and input to the beam splitter 701.

The three measurement lights scattered by the retina 120 and input to the beam splitter 701 and the three reference lights produced as a result of equally dividing the original reference light by three and subsequently input to the beam splitter 701 are synthetically combined by the beam splitter 701 to become interference lights. The interference lights directed to respective fiber collimators 611 are then input to optical fibers by the fiber collimators and entered to spectral detection sections 110 so as to be subjected to a spectral process and obtain OCT signals as in Example 1. On the other hand, the interference lights directed to an aluminum plate 702 are blocked by the aluminum plate that is treated to become black alumite because they are not necessary.

Thus, the present invention provides the above-described advantages regardless of the form of interferometer. While three lights are employed in each of the above-described examples, a similar effect can be achieved by using two or more than two lights other than three.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-013069, filed on Jan. 23, 2009, and Japanese Patent Application No. 2009-124135, filed on May 22, 2009, which are hereby incorporated by reference herein in their entirety.

The invention claimed is:

1. An imaging method for picking up an optical coherence tomographic image of an object using combined lights obtained by combining a plurality of return lights from the object irradiated with the plurality of measurement lights with the plurality of reference lights corresponding to the plurality of measurement lights, respectively, the method comprising:
    a step of irradiating different spot positions in the object with the plurality of measurement lights;
    a step of scanning the plurality of measurement lights such that irradiation spots of the plurality of measurement lights are apart in a direction intersecting with a main scanning direction, by a length not greater than the sum of diameters of the spots;
    a step of forming the optical coherence tomographic image of the object based on the combined lights and a displacement amount between the different spot positions in a plane scanned with the plurality of measurement lights;
    a step of detecting interference signals from the respective combined lights; and
    a step of executing an arithmetic process on the detected interference signals based on a displacement amount between different spot positions, using interference signals corresponding to at least two of the spot positions out of the interference signals corresponding to the respective spot positions and the displacement amount between the at least two spot positions, to thereby improve the signal-to-noise ratio as compared to using only one of the interference signals corresponding to the at least two spot positions.

2. The imaging method according to claim 1, wherein the step of executing an arithmetic process includes a step of executing an addition process or an averaging process using interference signals from spot positions located substantially one on the other in the direction perpendicular to the scanning direction in the scanning region.

3. The imaging method according to claim 2, wherein the step of executing an averaging process is a step of executing a weighting and averaging process using interference signals from spot positions located substantially one on the other in the direction perpendicular to the scanning direction in the scanning region.

4. The imaging method according to claim 3, wherein the step of executing a weighting and averaging process includes a weighting step using values corresponding respectively to light quantities of spots, signal intensity levels or noise levels.

5. A non-transitory computer-readable storage medium for storing a program for causing a computer to execute an optical tomographic imaging method according to claim 1.

6. An imaging apparatus for picking up an optical coherence tomographic image of an object using combined lights obtained by combining a plurality of return lights from the object irradiated with the plurality of measurement lights with the plurality of reference lights corresponding to the plurality of measurement lights, respectively, the apparatus comprising:
- an irradiation unit for irradiating different spot positions generally in the same predetermined layer to be scanned of the object with the plurality of measurement lights;
- a scanning unit for scanning the predetermined layer with the plurality of measurement lights along main scanning lines running generally in the same direction as corresponding to the respective measurement lights;
- a control unit for controlling the scanning unit such that proximate ones of the main scanning lines overlap with each other;
- an interference detecting unit for detecting interference signals from the respective combined lights; and
- wherein the signal processing unit executes an arithmetic process on the detected interference signals based on a displacement amount between different spot positions, using interference signals corresponding to at least two of the spot positions out of the interference signals corresponding to the respective spot positions and the displacement amount between the at least two spot positions, to thereby improve the signal-to-noise ratio as compared to using only one of the interference signals corresponding to the at least two spot positions.

7. The imaging apparatus according to claim 6, wherein the scanning unit includes a mechanism capable of varying the scanning speed.

8. An imaging apparatus for picking up an optical coherence tomographic image of an object using combined lights obtained by combining a plurality of return lights from the object irradiated with the plurality of measurement lights with the plurality of reference lights corresponding to the plurality of measurement lights, respectively, the apparatus comprising:
- an irradiation unit for irradiating different spot positions in the object with the plurality of measurement lights;
- a scanning unit for scanning the plurality of measurement lights such that irradiation spots of the plurality of measurement lights are apart in a direction intersecting with a main scanning direction, by a length not greater than the sum of diameters of the spots;
- a signal processing unit for forming the optical coherence tomographic image of the object based on the combined lights and a displacement amount between the different spot positions in a plane scanned with the plurality of measurement lights;
- an interference detecting unit for detecting interference signals from the respective combined lights; and
- wherein the signal processing unit executes an arithmetic process on the detected interference signals based on a displacement amount between different spot positions, using interference signals corresponding to at least two of the spot positions out of the interference signals corresponding to the respective spot positions and the displacement amount between the at least two spot positions, to thereby improve the signal-to-noise ratio as compared to using only one of the interference signals corresponding to the at least two spot positions.

9. An imaging method for picking up an optical coherence tomographic image of an object using combined lights obtained by combining a plurality of return lights from the object irradiated with the plurality of measurement lights with the plurality of reference lights corresponding to the plurality of measurement lights, respectively, the method comprising:
- a step of irradiating different spot positions generally in the same predetermined layer to be scanned of the object with the plurality of measurement lights;
- a step of scanning the predetermined layer with the plurality of measurement lights along main scanning lines running generally in the same direction as corresponding to the respective measurement lights;
- a step of controlling the scanning unit such that proximate ones of the main scanning lines overlap with each other;
- a step of detecting interference signals from the respective combined lights; and
- a step of executing an arithmetic process on the detected interference signals based on a displacement amount between different spot positions, using interference signals corresponding to at least two of the spot positions out of the interference signals corresponding to the respective spot positions and the displacement amount between the at least two spot positions, to thereby improve the signal-to-noise ratio as compared to using only one of the interference signals corresponding to the at least two spot positions.

10. A non-transitory computer-readable storage medium for storing a program for causing a computer to execute an optical tomographic imaging method according to claim 9.

11. The imaging method according to claim 1, wherein the object is the retina of an eye.

12. The imaging apparatus according to claim 6, wherein the object is the retina of an eye.

13. The imaging apparatus according to claim 8, wherein the object is the retina of an eye.

14. The imaging method according to claim 9, wherein the object is the retina of an eye.

* * * * *